United States Patent [19]
Childs et al.

[11] Patent Number: 5,766,962
[45] Date of Patent: Jun. 16, 1998

[54] DEVICE FOR COLLECTING AND TESTING SAMPLES

[75] Inventors: Mary Ann Childs, Baltimore; Mohammed A. Chowdhury, Greenbelt; David Bernstein, Eldersburg; Gregory K. Shipman, Baltimore; Erick Gray, Columbia, all of Md.

[73] Assignee: Universal Healthwatch, Inc., Columbia, Md.

[21] Appl. No.: 577,128

[22] Filed: Dec. 22, 1995

[51] Int. Cl.$^6$ .................. G01N 33/543; G01N 21/00; G01N 31/22; G01N 33/53
[52] U.S. Cl. .................. 436/518; 422/56; 422/58; 422/61; 422/255; 422/261; 422/278; 435/7.1; 435/7.93; 435/7.94; 435/7.95; 435/970; 435/810; 436/518; 436/530; 436/807; 436/810; 604/1
[58] Field of Search ............... 422/56, 58, 61, 422/255, 261, 278; 435/7.1, 810, 7.93, 7.94, 7.95; 436/518, 530, 807, 810; 604/1

[56] References Cited

U.S. PATENT DOCUMENTS

| | | |
|---|---|---|
| 4,952,204 | 8/1990 | Korteweg . |
| 5,035,860 | 7/1991 | Kleingeld et al. . |
| 5,198,365 | 3/1993 | Grow et al. .................. 436/66 |
| 5,295,952 | 3/1994 | Pietrafitta . |
| 5,308,580 | 5/1994 | Clark . |
| 5,441,698 | 8/1995 | Norell . |

OTHER PUBLICATIONS

"An Immunoflourescent Test for Faecal Occult Blood", K.D. Vellacott et al., The Lancet, vol. 1 (1981) No. 8210.
"Detection of Rotavirus in Faecal Specimens by Enzyme Immunoassay, Latex Agglutination and Electron Microscopy", I. Julkunen et al., Scandinavian Journal of Infectious Diseases., vol. 17, No. 3, 1985.
"A Novel Kit for Rapid Detection of Vibrio Cholerae 01", J.A.K. Hasan et al., Journal of Clinical Microbiology., vol. 32, No. 1, Jan. 1994.

*Primary Examiner*—Christopher L. Chin
*Assistant Examiner*—Bao-Thuy L. Nguyen
*Attorney, Agent, or Firm*—Foley & Lardner

[57] ABSTRACT

Improved devices for collecting and analyzing samples of aqueous solutions, body fluids, sewage or fecal matter to be used in detecting microbes and microbial byproducts. A device in accordance with the invention comprises a body including an internal channel having an entryway, a solute chamber connected to the entryway, a solute-adding mechanism operatively connected to the solute chamber, a window in the body that allows viewing of a portion of the channel, and an aperture in the body that opens to the channel; a bendable tang connected to the body; and a sample collection unit attached to the tang.

18 Claims, 4 Drawing Sheets

DEVICE FOR COLLECTING AND TESTING SAMPLES

FIELD OF THE INVENTION

This invention relates to improved devices for collecting and analyzing samples of aqueous and non-aqueous solutions, body fluids, sewage or fecal matter to be used in detecting microbes and microbial byproducts. In particular, this invention relates to devices for collecting samples of solutions or other matter suspected of containing cholera microbes or cholera microbe portions or byproducts such as antigens shed therefrom for immunoassay. The device is applicable also to the detection of HIV, hepatitis and other diseases and conditions which shed antigens into body fluids.

BACKGROUND OF THE INVENTION

Aqueous fluids such as rivers, streams, sewage effluents, sputum and fecal (or stool) samples are routinely tested for the presence of viruses, bacteria, parasites, other organisms, and antigens shed from such organisms. Methods for conducting such assays often begin with the collection of a sample from the suspected fluid or matter. The collection of aqueous fluids, fecal matter, or stool, usually requires a number of sample manipulation steps and typically concludes with the formation of colored indicator to indicate the presence or absence of a test analyte such as cholera toxin.

Aqueous fluid or stool collection is usually non-invasive and is ideal for obtaining samples of certain digestive disease organisms such as salmonella and cholera. Aqueous fluid or stool can be collected with a swab during investigation and applied directly to a test surface or volume.

Traditional methods and devices for investigating fecal matter and aqueous solutions suspected of containing cholera microbes or their byproducts have used complex chemical and microbiological assays. These traditional methods are being replaced with immunoassay methods. An advantage of immunoassay methods is that they are highly sensitive and require only a small sample volume. Some immunoassay methods, such as latex agglutination and enzyme immunoassay, can be performed with test kits that contain vials and reagent solutions that are combined in a particular way to obtain a test result.

Many immunoassay methods do not require electronic instrumentation or educated technicians or clinicians for their use. However, test kits that contain vials and reagent solutions are often not easily usable in underdeveloped areas of the world where modern devices and techniques are poorly understood. Even the simplest immunoassay usually require timed addition of reagents to test samples and the manipulation of plastic test parts that have to be brought together in a proper order. Similarly, such kits are not easily usable by people who are themselves sick and need to conduct diagnostic assays under exigent conditions. Such exigent conditions include those common to soldiers in the field, refugees from war, and victims of natural disasters such as earthquakes or hurricanes where water supplies are often contaminated.

The application of immunoassay techniques to fecal analysis in particular is difficult for several reasons. Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician.

However, stool samples have to be processed before their use in conventional immunoassays in order to remove interferences. This processing can cause complexity within the test method and prevents more widespread use of cholera tests in rural and lesser developed regions where machinery and reagents for processing are non-existent. Therefore, any reduction in the number of steps required to perform a fecal test and any reduction in contact between test operator and the test material would help to increase the early detection and consequently decrease in the spread of a disease, particularly where an agent such as cholera is involved.

Attempts have been made to alleviate the methodology problem of handling stool specimens. For example, M. A. Grow et al. in U.S. Pat. 5,198,365 describe a fecal sample handling method for a hemoglobin immunoassay that requires dilution of a stool specimen by 10 to 100 fold. Although dilution can possibly simplify the assay procedure, it lowers sensitivity by a dilution factor. A 10 to 100 fold dilution step is particularly unacceptable for many tests of infectious agents such as cholera because greater test sensitivity is desired to detect these agents at earliest clinical time periods.

On the other hand, if a sample is tested without a significant dilution (i.e. more than 3 fold) then a centrifugation and/or filtering step is generally required as described by Vellacott et al. in the LancetJan. 3 issue (1981) and by Jikunen et al. in the Scand. J. Infect. Dis.17: 245 (1985).

A recent attempt to eliminate the complexity problem in testing stool specimens was described in J. Clin. Micro.32: 249 (1994) by J. A. K. Hasan et al. This reference cites a rapid calorimetric immunodiagnostic kit for the detection of the presence of Vibrio cholera01 in clinical specimens.

In the procedure a stool specimen is passed through a filter that is separate from other kit components. Four drops of the stool filtrate are added to two drops of reconstituted gold labeled anti-vibrio cholera antibody. A swab is first added to the solution and then placed in an immunoassay testing device. Within the device, formed immune complexes are captured on a porous membrane that contains immobilized anti-vibrio cholera antibody.

Unfortunately, the separate filtration step in this procedure prolongs the test. The test is too complex for many untrained people and requires separate manipulation of two vials, one vial cap, a swab and an immunoassay device. Furthermore, test kits and methods that require many manipulations have more sources of error which lead to higher error rates. Finally, manufacturing costs increase when multiple parts and separate reagents are added to test kits.

Thus, a need exists for fecal test devices which are reliable and which can be used by untrained personnel or in exigent circumstances.

SUMMARY OF THE INVENTION

Accordingly, it is an object of the invention to eliminate or reduce the complexity of methods and kits for testing fecal samples.

A second object of the invention is to help limit fecal contamination of the test user and thereby decrease the spread of disease through the testing process itself.

Yet a third object of the invention is to decrease the cost of manufacturing and of using fecal test kits.

Yet another object of the invention is to improve the reliability of fecal test kits and methods by making them simpler to use.

A similar object of the invention is to provide a device with which an immunoassay strip can be reliably used.

In accordance with these and other objectives of the invention, a device for collecting a sample to be assayed for an analyte is provided. The device comprising a body including an internal channel having an entryway, a solute chamber connected to the entryway, a solute-adding mechanism operatively connected to the solute chamber, a window in the body that allows viewing of a portion of the channel, and an aperture in the body that opens to the channel; a bendable tang connected to the body; and a sample collection unit attached to the tang.

This embodiment of the invention also provides that the sample collection unit is displaceable from a first position remote from the aperture to a second position in the aperture so that a collection end of the sample collection unit enters the channel.

For purposes of this invention "analyte" is any substance to which a specific antibody can be made and whose detection in a fecal sample is desired. Infectious organisms that can be found within the digestive tract of humans and other animals typically are shed, or parts thereof are shed into the digestive tract and can be found in feces, sputum and in other body fluids. A preferred antigen is a molecule that is unique to a pathogenic organism and to which two antibodies can be bound.

A fecal, or stool sample is a portion of stool obtained from a human or other animal that is capable of harboring the pathogenic organism sought to be detected.

In accordance with other aspects of the invention, a solute charge is provided disposed within the solute chamber and the solute-adding mechanism further includes a trigger to release the solute charge into the entryway to the channel.

In accordance with additional objects of the invention, a diagnostic strip is provided disposed within the channel and is extended into the entryway.

In accordance with still other objects of the invention, the window allows viewing of at least one indicator region of the diagnostic strip. A diagnostic test strip suitable for the present invention will detect antigen from an aqueous sample that contacts it. Detection is carried out by the formation or disappearance of color from at least one region of the test strip.

In accordance with still other objectives of the invention, the bendable tang is integral with the body and is of sufficient longitudinal length the collection unit is placeable in the second position within the aperture.

To satisfy other aspects of the invention, the tang comprises a cleaner that removes excess sample from the sample collection unit. The sample collection unit is substantially cylindrical and the cleaner comprises a sleeve with an orifice slidably disposed about the tang. The orifice is dimensioned so that the sleeve can be removed from the tang by withdrawing the sleeve over the sample collection unit. The orifice is also provided with a lining of an adsorptive material. The lining contacts the sample collection unit when the sleeve is withdrawn from the tang over the unit.

In accordance with yet additional objects of the invention, the solute comprises an extraction reagent comprises an aqueous solution of at least one detergent and at least one buffer.

The extraction reagent is an aqueous fluid that comprises at least one buffer and at least one detergent. The buffer is in a concentration between 1 mM and 1M and more preferably in a concentration of between 5 mM and 250 mM. The buffer pH is between pH 3 and 13 and more preferably between pH 6 and pH 9. The buffer composition can be one or more chemical compounds which are known to an average skilled worker in the art. The detergent is an amphoteric compound, many of which are known to an average skilled worker in the art. Examples of detergents are: deoxycholate, Tween-20, triton X-100, and sodium docedyl sulfate. The detergent is in a concentration between its critical micelle concentration and 10% wgt/vol.

For extraction of some analytes, the extraction buffer preferably comprises protein as well. Bovine serum albumin, hydrolysed casein and the like are suitable in the concentration of between 0.01% to 10% (wt/vol) and more preferably between 0.1 and 5% (wt/vol).

The extraction buffer is preferably optimized for a test for a particular disease causing organism although preferably, a composition is chosen that can be used for more than one organism. Most preferably, the detergent and detergent concentration chosen will release at least some lipopolysaccharide from the surface of a gut bacterium for testing of pathogenic gut bacteria such as those responsible for cholera and salmonella.

In accordance with yet additional aspects of the invention, the trigger comprises a thinned portion of the body the sample collection pad comprises an adsorbent pad.

As a result of these improvements, the cost of manufacturing a fecal test device is decreased and operator training requirements are relaxed. Furthermore, operation of the test poses less risk of contamination from samples that are potentially infected with infectious disease agents.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

Detailed Description of the Preferred Embodiments

Figure 1:
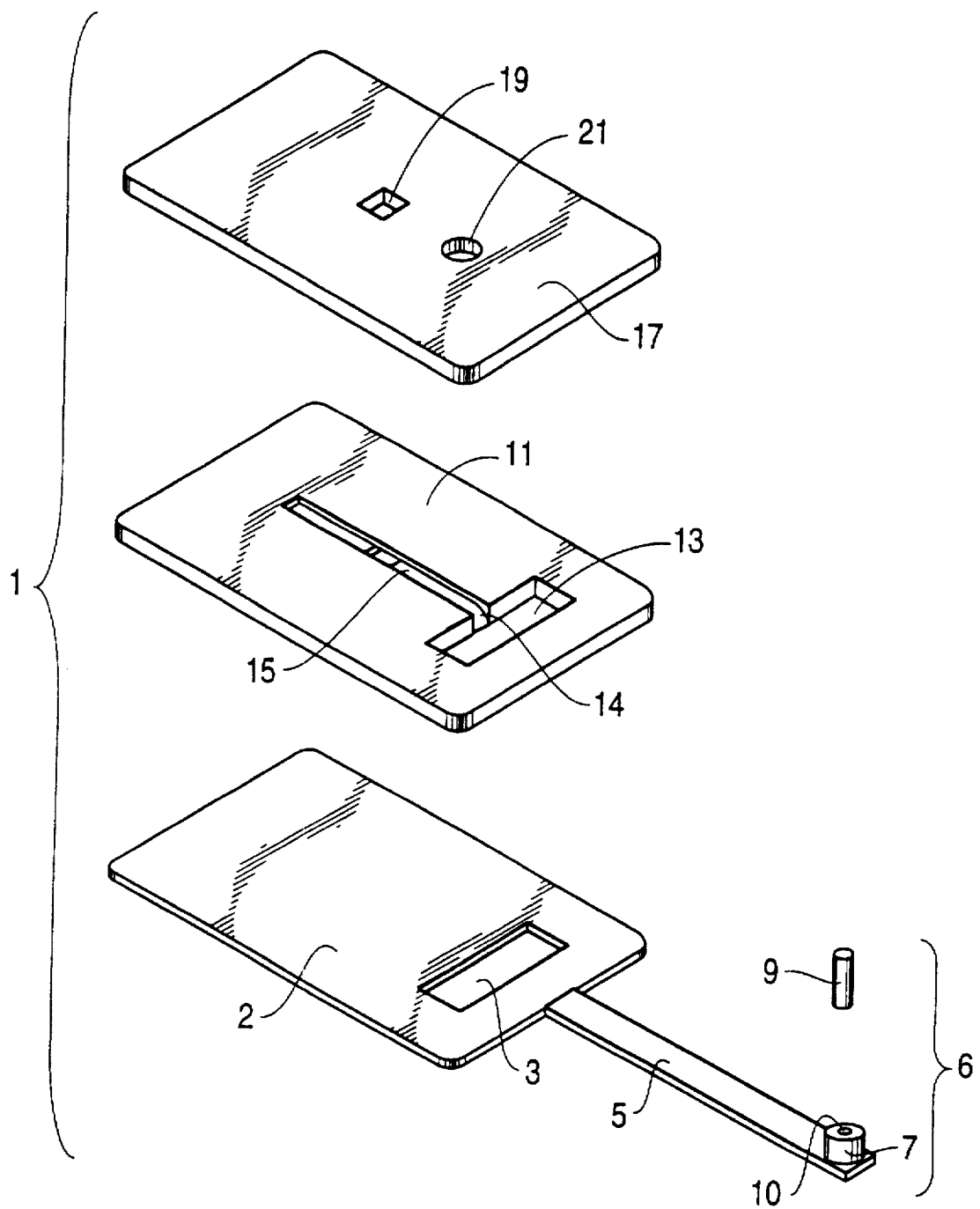
FIG. 1 shows an exploded view of the first preferred embodiment of the invention.

The present invention uses a molded or formed body of plastic or other suitable medical or diagnostic grade material having formed therein a chamber suitable for storing a solute, a channel suitable for holding a diagnostic amino assay strip, wherein the channel and chamber are connected by an entryway, a sample aperture disposed to permit access to the diagnostic strip, and a window for viewing a portion of the strip having a calorimetric or other indicator thereon. According to the invention, the device is provided also with a solute charge housed in solute chamber and a trigger for releasing the solute through the entryway onto the diagnostic strip. In some embodiments of the invention, a part of the body forming a wall of the solute chamber is thinned so that the trigger for activating release of the solute can be accessed by deforming the thinned portion.

The body is provided with a tang, preferably having two ends, being attached by one end to the body and having a sample collection unit attached to the second end. The tang is of a bendable or pliable material so that after the sample collection unit is contacted with a fecal sample, or an aqueous sample such as that which might be obtained from a stream, sewage, sputum, or civil engineering effluent, that can be inserted into a sample aperture to thereby contact the diagnostic strip with a portion of the collected sample. In one preferred embodiment of the invention, the relative dimensions of the sample aperture and the sample collection unit are such that the collection unit is irreversibly captured by the sample aperture to thereby decrease opportunity for spread of infectious material.

The tang is of sufficient length so that it can be bent to permit insertion of the sample collection unit into the sample aperture in the body of the invention. In some preferred embodiments of the invention, the sample tang is of sufficient length, for example, in excess of 6 inches, so that the sample collection unit can be dipped into a fluid suspected of harboring a particular analyte without exposing the user to the fluid. The tang is formed of pliable or bendable materials such as medical grade polypropylene or other materials as well known in the trade.

Alternatively, the tang is provided with a snap fit connection with the body or a breakable connection so that the tang is removable from the body. This feature allows a user to use the tang seperate from the body and then place the sample collection unit into the aperture of the body.

In other preferred embodiments of the invention, the collection unit is provided with a cleaner that cleans excess sample from the tang and/or the sample collection unit before sample collection unit is inserted into the aperture in the body. In one preferred embodiment of the invention, the cleaner is a sleeve slidably disposed on the tang, and provided with absorbent on its internal surfaces so that when the cleaning sleeve is removed from the tang by sliding it over the collection unit, excess material is absorbed within the sleeve to thereby decrease contamination of the user or other surfaces with these sample material.

In yet another preferred embodiment of the invention, the sleeve can be provided with fracture indentations so that it may be easily spread apart for access to the sample portions contained therein. In accordance with this aspect of the invention, the sleeve and body of individual units of the invention can be given identical numbers so that the extra sample material contained within the sleeve may be stored as a parallel sample for later use or confirmation tests.

The present invention can be more fully appreciated with reference to the above-noted figures and to the following detailed description of those figures. In connection with the foregoing figures, like reference numerals will refer to like portions thereof.

FIG. 1 shows a device for collecting a sample to be assayed for an analyte having body 1. The body 1 includes three separate plates 2, 11, and 17 which are shown in a perspective view with space in between to show the detailed aspects thereof. Base plate 2 has thinned section 3 that serves as one example of a solute-adding mechanism to trigger the release of a solute charge. Base plate 2 and, thus, body 1, has a tang 5 attached thereto. At the portion of tang 5 located most distal from base plate 2, tang 5 is provided with a sample collection unit 6. The sample collection unit 6 has a collection pad holder 7. Collection pad holder 7 is provided with collection pad holder void 10 for holding a sample collection pad 9. The sample collection unit 6 is arranged on the tang 5 so that a central axis of the sample collection unit 6 is perpendicular with a longitudinal axis of the tang 5.

When assembled, the sample collection pad 9 is disposed securely in collection pad holder void 10. Depending upon the analytes to which the invention is directed, collection pad 9 is of absorbent or adsorbent material suitable for gathering and holding an aqueous or fecal sample.

The middle plate 11 is provided with a solute chamber 13, a diagnostic strip channel 15, and an entryway 14 communicating therebetween. Top plate 17 is provided with window 19 disposed over diagnostic strip channel 15 so that visual observations can be made of at least part of an indicating portion of a diagnostic strip disposed within channel 15. The window 19 that allows viewing of a portion of the diagnostic strip channel 15. Preferably, the window 19 is disposed over at least part of a colorimetric indicating portion of a diagnostic strip disposed within the diagnostic strip channel 15.

Top plate 17 is also provided with aperture 21 of suitable dimensions for receiving the sample collection unit 6. In a preferred embodiment of the invention, once the collection pad holder 7 having sample collection pad 9 securely disposed therein is installed into the aperture 21, the sample collection unit 6 is locked in the aperture 21. The sample collection unit 6 can be locked into the aperture 21 by any suitable arrangement such as a groove and a detent or a press fit.

Figure 2:
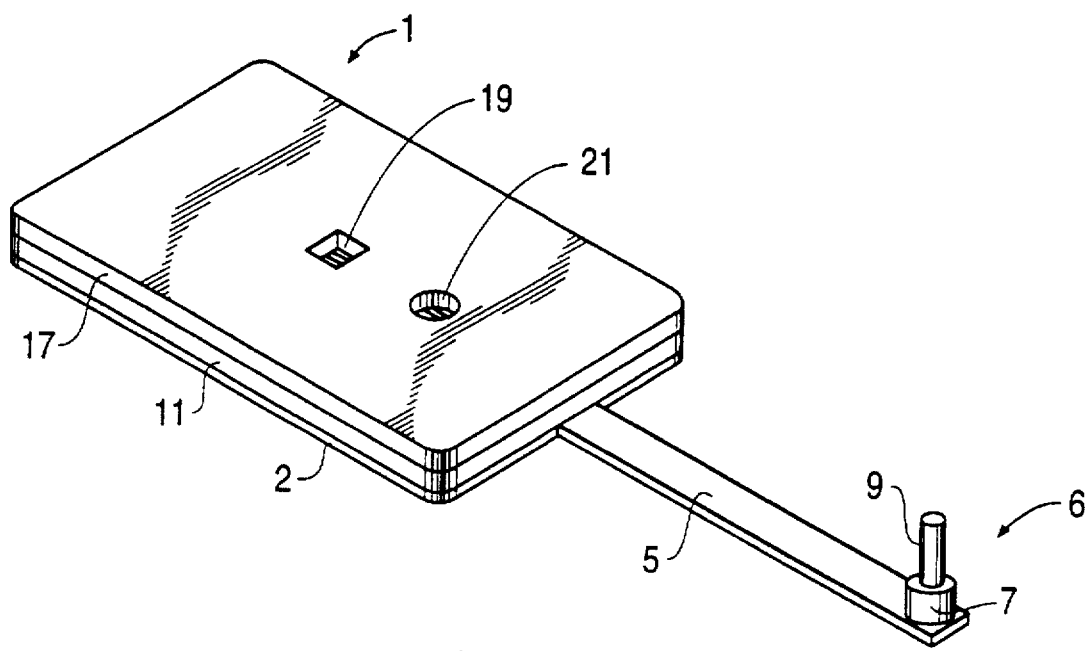
FIG. 2 shows an assembled version of the invention shown in FIG. 1.

As shown in FIG. 2, the body 1 includes base plate 2, middle plate 11, and top plate 17 that are adhered to one another by an adhesive, plastic welding, lamination, or by other means known in the art. When the base plate 2, middle plate 11, and top plate 17 that are adhered to one another the solute chamber 13, entryway 14 and diagnostic strip channel 15 are formed. The solute chamber 13, the entryway 14, the diagnostic strip channel 15 communicate with one another and are each sealed in a fluid proof manner at their junctions with the adjoining plates. As shown in FIG. 1, the aperture 21 is disposed over channel 15 to permit contact of collection pad 9 with a diagnostic strip (not shown) disposed within the diagnostic strip channel 15 when the sample collection device is in a position in the aperture 21.

Figure 3:
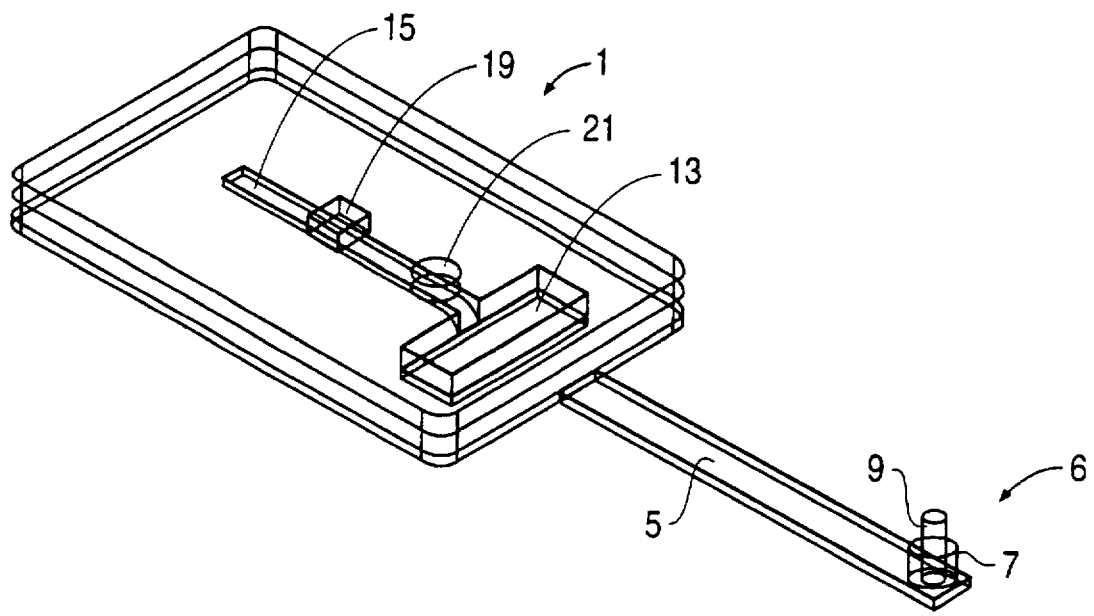
FIG. 3 shows a transparent view of the device shown in FIG. 2.

In use, as shown in FIGS. 1–3, the collection pad 9 is contacted with a fecal sample or an aqueous fluid, such as fluids for toilet water to obtain a sample to be tested. Collection pad holder 7, having collection pad 9 securely fastened therein and having a sample thereon is then directed into aperture 21, thus bending tang 5. As discussed above, in one preferred embodiment of the invention, the relative dimensions of collection pad 9 and collection pad holder 7 is such that there are irreversibly captured in aperture 21 and the sample disposed on collection pad 9 enters the diagnostic strip channel 15 to engage a diagnostic strip. A solute charge (not shown) contained in a plastic bag (not shown) disposed in solute chamber 13 is then ruptured by pressure applied through thinned section 3 of base plate 2. The solute charge (not shown) then has access to diagnostic strip channel 15 through entryway 14 and flows along the diagnostic strip (not shown) in a direction away from solute chamber 13 to elute the sample placed upon the diagnostic strip by collection pad 9. The eluted sample is thus carried in a direction away from solute chamber 13 through an indicating region of the diagnostic strip to thereby contact the sample with reagents contained in the indicating region of the strip. After a sufficient period of time, results in the indicating region of the diagnostic strip can be viewed through window 19.

FIG. 3 shows a transparent view of the device shown in FIG. 2. This view illustrates the relative relationship and positions of the diagnostic strip channel 15, solute chamber 13, aperture 21, and window 19 within the body 1. FIG. 3 also shows the relative positions of the collection pad holder 7, the void 10, and the sample collection pad 9 of the sample collection unit 6.

Figure 4:
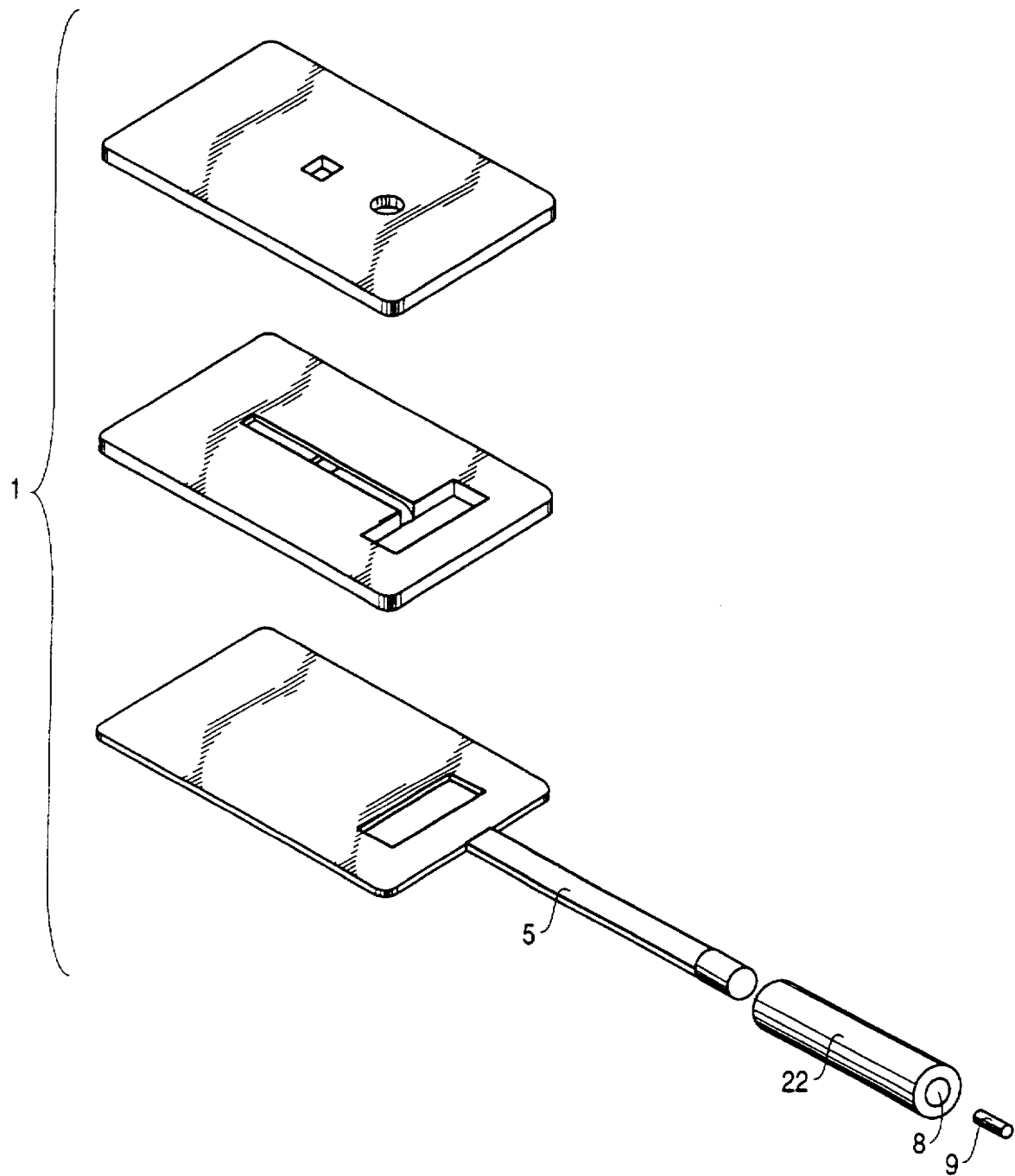
FIG. 4 shows an exploded view of a second embodiment of the invention.

FIG. 4 shows a second embodiment of the invention. In this embodiment of the device for collecting a sample to be assayed for an analyte, the tang 5 is provided with axially parallel sample collection unit 6 and with cleaning sleeve 22. This arrangement provides that the tang 5, the collection pad holder 7, the collection pad 9, and the cleaning sleeve 22 are axially aligned. Cleaning sleeve 22 is provided with cleaning sleeve orifice or aperture 8 of a sufficient dimension so that cleaning sleeve 22 can slide over collection pad holder 7 during assembly.

Figure 5:
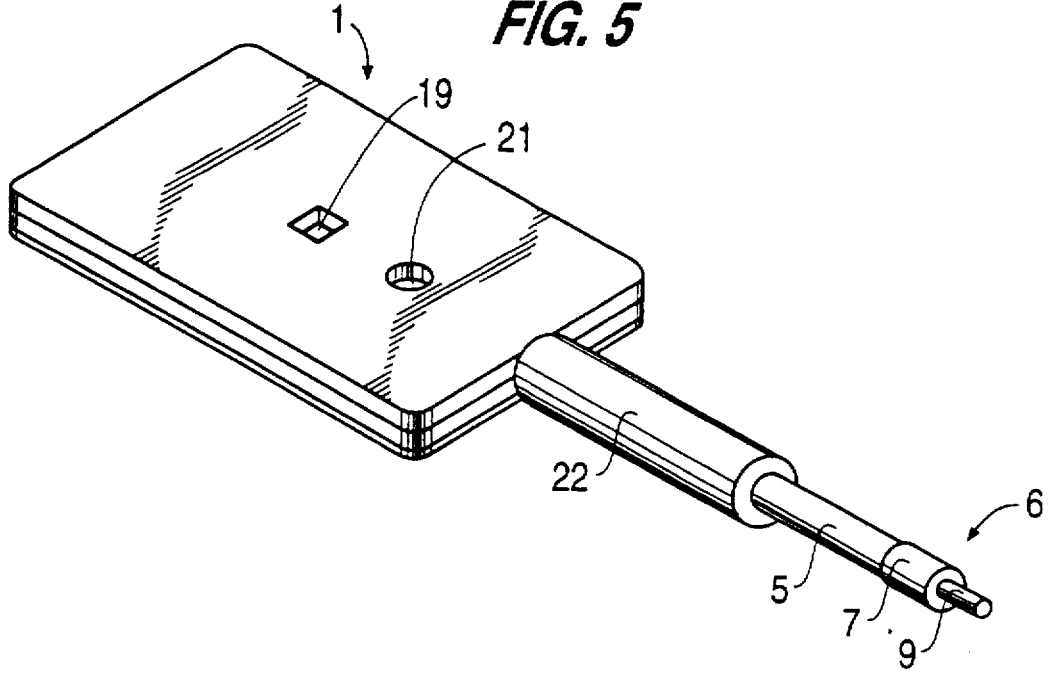
FIG. 5 shows the assembled version of the invention shown in FIG. 4.

Referring to FIG. 5, cleaning sleeve 22 is shown disposed about tang 5 between body 2 and sample collection unit 6. In operation of the invention, collection pad 9 is contacted with a fecal sample or aqueous solutions suspected of containing a pathogen. Cleaning sleeve 22, having absorbent material disposed therein (not shown), is then slid along tang 5 in a direction away from body 2 to pass over collection pad holder 7 and collection pad 9 to thereby remove any excess sample therefrom. After removal of cleaning sleeve 22, the sample collection unit 6 is directed into aperture 21 where it is irreversibly held with at least a portion of the sample contained upon collection pad 9 contacting the diagnostic strip held within diagnostic strip channel 15 disposed beneath window 19.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A device comprising:
   A) a body including:
      an internal diagnostic strip channel having an entryway,
      a solute chamber connected to the internal diagnostic strip channel by the entryway,
      a solute-adding mechanism comprising a thinned section of the body located on the bottom of the solute chamber,
      a window in the body that allows viewing of a portion of the internal diagnostic strip channel, and
      an aperture in the body having top and bottom openings that allows access to the internal diagnostic strip channel;
   B) a bendable tang connected to the body; and
   C) a sample collection unit attached to the tang;
wherein the sample collection unit is displaceable from a first position remote from the aperture to a second position in the aperture by bending the bendable tang so that a collection end of the sample collection unit enters the internal diagnostic strip channel.

2. The device of claim 1, further comprising a solute charge contained in a plastic bag disposed within the solute chamber, wherein the solute charge comprises an extraction reagent.

3. The device of claim 2, wherein the solute-adding mechanism comprising rupturing of the plastic bag by pressure applied through the thinned section of the solute chamber.

4. The device of claim 2, further comprising a diagnostic strip disposed within the internal diagnostic strip channel.

5. The device of claim 4, wherein the diagnostic strip extends into the entryway.

6. The device of claim 5, wherein the window allows viewing of at least one indicator region of the diagnostic strip.

7. The device of claim 1, wherein the bendable tang is integral with the body.

8. The device of claim 1, wherein the bendable tang has a longitudinal length so that the sample collection unit is placeable in the second position in the aperture without removal of the bendable tang from the body.

9. The device of claim 1, wherein the tang includes a cleaner.

10. The device of claim 1, wherein the sample collection unit is cylindrical.

11. The device of claim 9, wherein the cleaner comprises a sleeve having two orifices, the sleeve being slidably disposed about the tang.

12. The device of claim 11, wherein the two orifices are dimensioned so that the sleeve is removable from the tang by withdrawing the sleeve over the sample collection unit.

13. The device of claim 11, wherein the two orifices are provided with an absorptive lining.

14. The device of claim 4, wherein the diagnostic strip contains reagents for recognizing cholera antigens.

15. The device of claim 2, wherein the extraction reagent comprises an aqueous solution of at least one detergent and at least one buffer.

16. The device of claim 1, wherein the sample collection unit comprises an adsorbent pad.

17. A device comprising:
   A) a body including:
      an internal diagnostic strip channel having an entryway,
      a solute chamber connected to the internal diagnostic strip channel by the entryway,
      a solute charge comprising an aqueous solution of at least one detergent and at least one buffer contained in a plastic bag disposed within the solute chamber,
      a solute-adding mechanism comprising a thinned section of the body located on the bottom of the solute chamber, the solute-adding mechanism comprising rupturing of the plastic bag by pressure applied through the thinned section of the solute chamber,
      a diagnostic strip disposed within the internal diagnostic strip channel that extends into the entryway,
      a window in the body that allows viewing of at least one indicator region of the diagnostic strip, and
      an aperture in the body having top and bottom openings that allows access to the internal diagnostic strip channel;
   B) a bendable tang connected to the body, he bendable tang being integral with the body and comprising a cleaving sleeve that slides about the tang; and
   C) a sample collection unit connected to the tang, the collection unit comprising an adsorbent pad;
wherein the sample collection unit is displaceable from a first position remote from the aperture to a second position in the aperture by bending the bendable tang so that a portion of the absorbent pad enters the internal diagnostic strip channel.

18. The device of claim 17, wherein the diagnostic strip contains reagents for recognizing cholera antigens.

* * * * *